United States Patent [19]
März et al.

[11] Patent Number: 4,824,433
[45] Date of Patent: Apr. 25, 1989

[54] PUNCTURING AND CATHETERIZING DEVICE FOR THE HUMAN OR ANIMAL BODY

[75] Inventors: Peter März; Jürgen Postel, both of Munich, Fed. Rep. of Germany

[73] Assignee: Sterimed Gesellschaft für medizinischen Bedarf mbH, Saarbrücken, Fed. Rep. of Germany

[21] Appl. No.: 604,651

[22] Filed: Apr. 5, 1984

[30] Foreign Application Priority Data

Aug. 6, 1982 [DE] Fed. Rep. of Germany ....... 3239466

[51] Int. Cl.⁴ .............................................. A61M 5/00
[52] U.S. Cl. ...................................... 604/21; 604/164; 128/741
[58] Field of Search ..................... 604/164, 20, 22, 40, 604/52, 161, 163, 170, 21, 117; 128/635, 642, 741, 419

[56] References Cited

U.S. PATENT DOCUMENTS

| | | | |
|---|---|---|---|
| 2,522,052 | 9/1950 | Logan et al. | 128/741 |
| 3,087,486 | 4/1963 | Kilpatrick | 128/642 |
| 3,098,813 | 7/1963 | Beebe et al. | 128/635 |
| 3,249,103 | 5/1960 | Woodhouse | 128/635 |
| 3,406,685 | 10/1968 | May | 604/170 |
| 3,682,162 | 8/1972 | Colyer | 128/642 |
| 4,128,173 | 12/1978 | Lazarus | 206/570 |

Primary Examiner—Stephen C. Pellegrino
Attorney, Agent, or Firm—Toren, McGeady & Associates

[57] ABSTRACT

Puncturing and catheterizing device for the human or animal body with a metallic puncture needle and a cannula which surrounds the puncture needle in the region between its point and rear end and through which, after the puncture needle has been pulled out, a longer guide-wire can be inserted into the body, which then, after the cannula has also been pulled out, serves as a guide for a catheter to be inserted. The puncture needle 3 is electrically conductive from its point 1 to its end projecting out of the cannula 9 and is equipped with an electrical connecting piece 5 at the rear end (FIG. 1).

3 Claims, 2 Drawing Sheets

PUNCTURING AND CATHETERIZING DEVICE FOR THE HUMAN OR ANIMAL BODY

FIELD OF THE INVENTION

The invention relates to a puncturing and catheterizing device for the human or animal body with a metallic puncture needle and a cannula which surrounds the puncture needle in the region between its point and rear end and through which, after the puncture needle has been pulled out, a longer guidewire can be inserted into the body, which then, after the cannula has also been pulled out, serves as a guide for a catheter to be inserted.

PRIOR ART

Devices of this type are known as vein catheters. However, the known devices are not suitable for puncturing and catheterizing nerve tracts, since in such a procedure it is very difficult to insert the puncture needle correctly into the inside of the nerve sheath or into the space between the nerve sheath and nerve.

A combined puncture and injection needle for nerve tracts is known, which is also intended for insertion into the space between the nerve sheath and the nerve and, on its rear end, is connected to a flexible tube, which on the one hand is equipped with a connecting piece for injection syringes and furthermore itself has an electrical lead wire for connection to the pulser (neurotracer) used in the nerve exploration process. However, this known instrument permits only immediate injection of substances through the puncture needle, without there being a possibility of inserting a longer catheter into the space between the nerve sheath and the nerve for a longer period, after the puncture needle has been inserted.

DESCRIPTION OF THE INVENTION

The present invention is based on the object of taking measures with a device of the type in question in order to enable this to be used for puncturing and catheterizing nerve tracts.

The object is achieved by making the puncture needle electrically conductive from its point to its end projecting out of the cannula and equipping the rear end with an electrical connecting piece.

The insertion of nerve catheters can be substantially simplified with such an embodiment of the device. An electrical impulser such as is commercially available under the designation neurotracer can be connected to the electrical connecting piece of the puncture needle, and it thus becomes possible to feel the way exactly inside the nerve sheath with the puncture needle and the surrounding cannula and to establish undesirable deviations immediately. If an undesirable deviation occurs, the current pulse given no longer reaches the nerve and the physician performing treatment can immediately detect, by the reaction of the patient, that he must guide the needle elsewhere.

FIG. 1A shows schematically a drawing of a piece broken out of the cannula of the device from FIG. 1 with a guidewire (mandrin) passing through, which can be used for insertion of a nerve catheter.

FIG. 1B shows schematically, also on an enlarged scale, a piece of a nerve catheter to be inserted into the human body by means of the guidewire.

Figure 1:
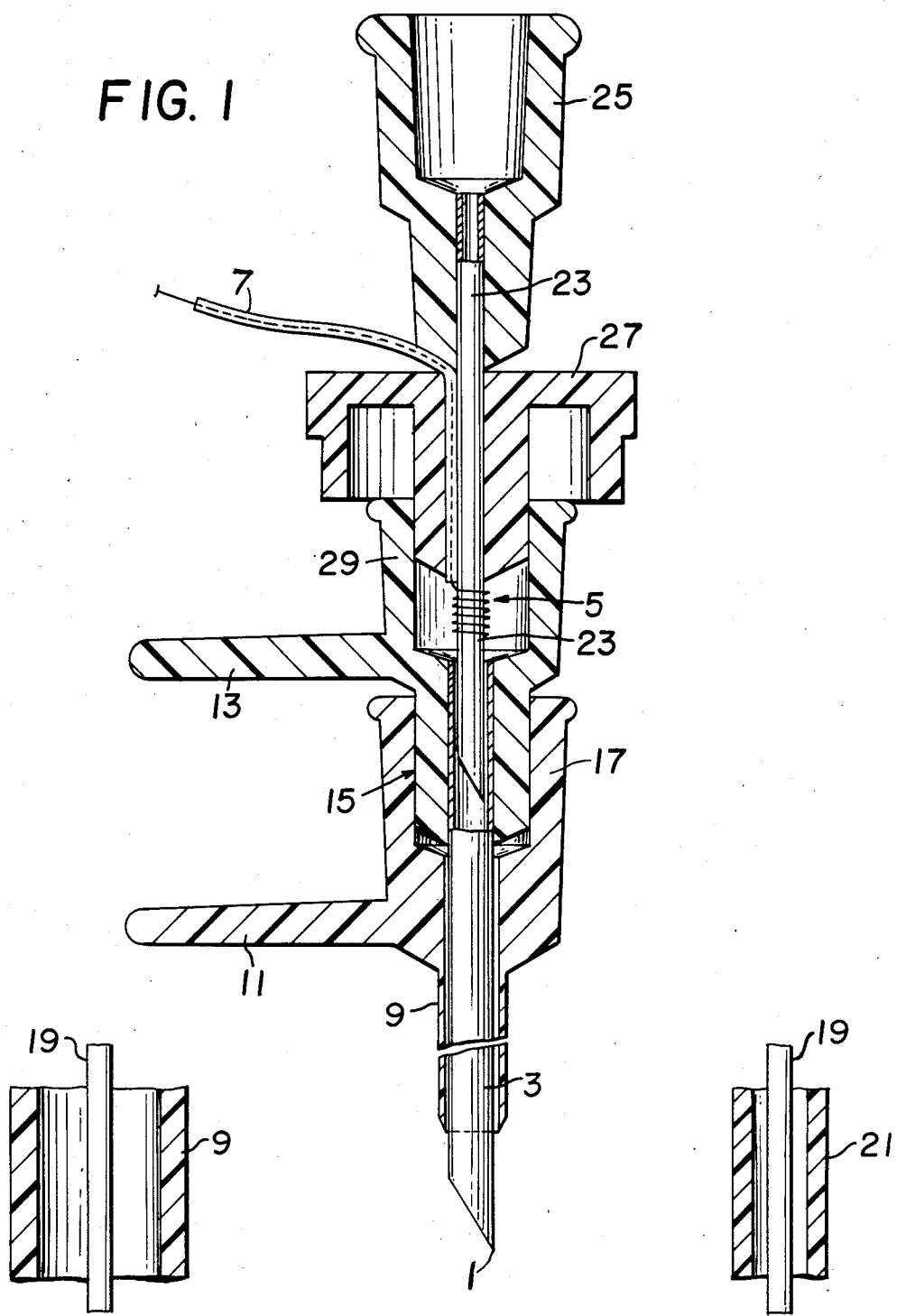
FIG. 1 shows, on an enlarged scale, a puncturing and catheterizing device for the human body with an electrical connecting piece for connection to an electrical pulser; the puncture needle and the surrounding cannula are shown broken off.

The puncturing and catheterizing device shown in the drawings can be used to establish a connection of the inside of a nerve sheath accommodating a nerve with the surrounding environment. In medical treatment, such a connection is used, for example, in order to catheterize the inside of the nerve sheath, infuse treatment agents or the like. For this purpose, relatively long catheters must also occasionally be inserted to sites deep within the body, as with the insertion of vein catheters.

The puncturing and catheterizing device shown has a puncture needle 3 which has a point 1, and which is, for example, 60 mm long and is suitable for insertion into the body in the same way as the needle of an injection syringe.

The puncture needle consists of electrically conductive material and has at its rear end an electrical connecting piece 5, which is to be described in more detail and is equipped with an electrical connecting lead 7.

The puncture needle 3 can be connected onto an electrical pulser, which is not shown in more detail and is commercially available, for example, under the designation "neurotracer", by means of the electrical connecting lead 7. The pulse given by the electrical pulser enables the physician performing treatment to move the puncture needle 3 forwards inside the nerve sheath. As soon as the puncture needle 3 and its surrounding insulating cannula 9 has been inserted into the human body and has penetrated a nerve sheath, the current pulses passed in can act on the nerve and then lead to an externally visible motor reaction of corresponding parts of the body, for example the hand.

As long as the puncture needle remains in the nerve sheath, the electrical pulses passed in via the puncture needle remain effective for triggering off motor reactions of the part of the body. As long as these motor reactions are visible, the physician performing treatment knows that he has passed the puncture needle, and with it the cannula, correctly along the space between the nerve and nerve sheath.

Moreover, the puncture needle needs to be passed only a short way along the nerve sheath, and then already provides a sufficient guide for the cannula 9, which can then be pushed against the puncture needle 3 into the nerve sheath by means of the handling piece 11.

As shown, the cannula 9 is somewhat shorter than the puncture needle 3, so that the point 1 projects forwards out of the insulating cannula 9. The insulating cannula consists of a suitable plastic material and is also appropriately designed narrow, in order to facilitate insertion into a nerve sheath.

In order to facilitate the joint insertion of puncture needle 3 and cannula 9 initially required, a handling piece 13 at the rear end of the puncture needle 3 is pushed together telescopically, at 15, with a collar 17 at the rear end of the cannula 9, this push-fit connection easily being undone in order to push the cannula 9 forwards over the puncture needle 3 in the manner shown.

After the puncture needle 3 has been withdrawn, the collar 17 of the cannula 9 is used in the further treatment, and also for insertion of a guidewire 19, the so-called mandrin, which is shown schematically inside the cannula 9 in FIG. 1A and which, after the cannula 9 has also been withdrawn from the body, can also be used for insertion of a nerve catheter 21 in the manner indicated schematically in FIG. 1B. The guidewire 19 and nerve catheter 21 are, for example, 25 cm in length.

The electrical connecting piece shown in FIG. 1 has a metallic needle 23, which is inserted into the rear end of the puncture needle 1 and thus makes an electrically conductive connection. (The space shown is merely to enable the needles to be shown more clearly, and is in no way an insulating space).

The metallic needle 23 itself can also be a hollow needle and can be provided with a rear connecting piece 25, so that injections and the like can be carried out even when the electrical connection is made.

The metallic needle 23 is surrounded by a connecting plug 27, which can be pushed together with a connecting socket 29 on the rear handling part 13 of the puncture needle 3. The connecting plug 27 thereby at the same time serves to fix the electrical connecting lead 7 leading to the electrical pulser.

It goes without saying that the male cone of the connecting plug 27 fits tightly into the female cone of the connecting socket 29, so that suction can also be effected during the puncturing operation with an injection syringe mounted on the connecting piece 25.

Figure 2:
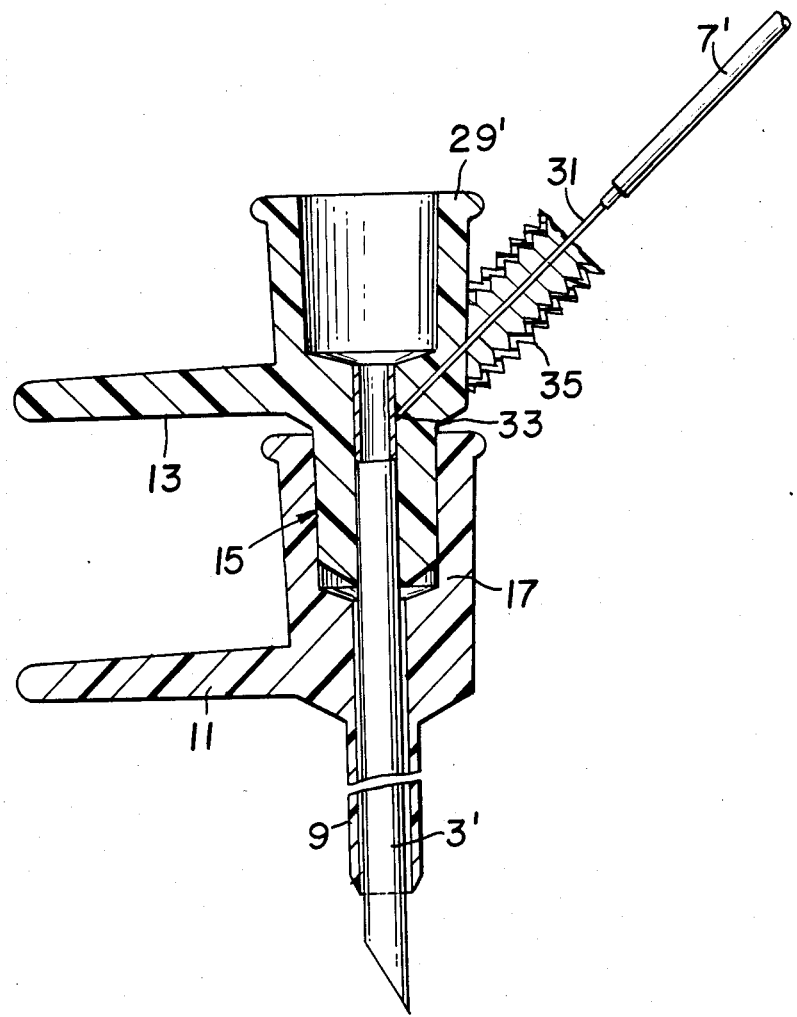
FIG. 2 shows schematically a puncturing and catheterizing device of the type shown in FIG. 1 with a different design of the electrical connecting piece and a flexible tube for sterile covering of the electrical connection lead.

As can be seen from FIG. 2, an electrical connection for the rear end of the puncture needle 3' can also be made by an arrangement in which an electrical conductor 31, which is connected electrically to the puncture needle at 33, is inserted through the side of the connecting socket 29' of the puncture needle. A simple connection to an electrical pulser can also be made in this manner, via lead 7'.

FIG. 2 also illustrates schematically the arrangement of a flexible tube 35 which can tightly surround the electrical conductor 31, and especially also its exit point, issuing from the connecting socket 29. This provides the possibility of keeping the electrical connecting pieces, such as the conductor 31 and the line 7', on the device itself short, and instead, with an appropriately long embodiment of the flexible tube 35, to bring the lead from the electrical impulser close up to the puncturing and catheterizing device in a sterile manner. This device can certainly be mass-produced under sterile conditions, and when used, it is necessary only to draw the flexible tube 35 over the lead from the electrical pulser so that the sterility of the environment is not endangered by this lead.

The electrical connecting piece at the rear end of the puncture and catheterizing device can also be realized in various other ways, which are not shown or described here in more detail.

Thus, for example, the electrical connection can be made by means of a so-called crocodile clip at an exposed piece provided for this at the rear end of the puncture needle.

We claim:

1. A puncturing and cathetering device for the human or animal body with a metallic puncture needle and a cannula which surrounds the puncture needle in the region between its point and rear end and through which, after the puncture needle has been pulled out, a longer guidewire can be inserted into the body, which then, after the cannula has also been pulled out, serves as a guide for a catheter to be inserted, wherein the puncture needle (3,3') is electrically conductive from its point (1) to its end projecting out of the cannula (9) and is equipped with an electrical connecting piece (5; 31,33) at the rear end and means for connecting the electrical connecting piece to an electrical source.

2. A device as claimed in claim 1, wherein the puncture needle, as known per se, is hollow and the electrical connecting piece (5) at the rear end is designed such that an unimpeded flow of liquid through the puncture needle is possibe.

3. A device as claimed in claim 2, wherein the electrical connecting piece is formed from a hollow metallic needle which can be inserted into the rear end of the puncture needle (3) and to which an electrical connecting lead (7) can be connected.

* * * * *

UNITED STATES PATENT AND TRADEMARK OFFICE
CERTIFICATE OF CORRECTION

PATENT NO. : 4,824,433
DATED : April 25, 1989
INVENTOR(S) : Peter März and Jürgen Postel It is certified that error appears in the above-identified patent and that said Letters Patent is hereby corrected as shown below:

Title page:

[21] Appl. No.: 604,651

[22] PCT filed: August 5, 1983

[86] PCT No. : PCT/EP83/00210

Sec. 371 Date: April 5, 1984

Sec. 102 Date: April 5, 1984

Signed and Sealed this

Twenty-third Day of January, 1990

Attest:

JEFFREY M. SAMUELS

*Attesting Officer*     *Acting Commissioner of Patents and Trademarks*